(12) United States Patent
Redepenning

(10) Patent No.: US 7,387,846 B2
(45) Date of Patent: Jun. 17, 2008

(54) ELECTROLYTIC DEPOSITION OF COATINGS FOR PROSTHETIC METALS AND ALLOYS

(75) Inventor: Jody G. Redepenning, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 11/254,710

(22) Filed: Oct. 21, 2005

(65) Prior Publication Data

US 2006/0099456 A1    May 11, 2006

Related U.S. Application Data

(62) Division of application No. 10/034,805, filed on Dec. 27, 2001, now Pat. No. 7,014,749.

(60) Provisional application No. 60/258,897, filed on Dec. 28, 2000.

(51) Int. Cl.
    *B32B 9/00* (2006.01)
    *A61L 33/00* (2006.01)
    *C25D 9/02* (2006.01)

(52) U.S. Cl. .................. 428/698; 428/699; 428/701; 427/2.24; 623/20.17; 623/23.36; 623/23.37; 623/23.56; 205/318

(58) Field of Classification Search ............ 428/698, 428/701; 427/2.24; 623/11.11, 20.17, 20.36, 623/20.37, 20.56; 205/318
    See application file for complete search history.

(56) References Cited

U.S. PATENT DOCUMENTS

| | | | |
|---|---|---|---|
| 4,264,422 A | 4/1981 | Funabashi et al. | |
| 5,166,187 A | 11/1992 | Collombel et al. | |
| 5,180,426 A | * 1/1993 | Sumita | 106/35 |
| 5,281,404 A | 1/1994 | Sumita | |
| 5,310,464 A | 5/1994 | Redepenning | |
| 5,413,693 A | 5/1995 | Redepenning | |
| 5,458,863 A | 10/1995 | Klassen | |

(Continued)

FOREIGN PATENT DOCUMENTS

EP    0 298 501 A2    1/1989

(Continued)

OTHER PUBLICATIONS

"In vitro properties of a chitosan bonded bone filling paste: studies on solubility of calcium phosphate compounds" Ito et al., Journal of Biomedical Materials Research; vol. 32, pp. 95-98. (1996).*

(Continued)

*Primary Examiner*—Callie Shosho
*Assistant Examiner*—Jonathan Langman
(74) *Attorney, Agent, or Firm*—Husch Blackwell Sanders; David H. Milligan; Sean P. Connolly

(57) ABSTRACT

An article coated with an electrolytically deposited bio-compatible composite layer useful as an internal prosthetic device is disclosed. The bio-compatible composite coating that is electrolytically deposited onto the article comprises hydroxyapatite and chitosan. The introduction of chitosan into the crystal matrix of brushite/hydroxyapatite significantly improves the adhesive and chemical and mechanical stability properties of the coating.

16 Claims, 4 Drawing Sheets

U.S. PATENT DOCUMENTS

| | | | |
|---|---|---|---|
| 5,605,713 | A | 2/1997 | Boltong |
| 5,618,339 | A | 4/1997 | Ito |
| 5,776,193 | A | 7/1998 | Kwan et al. |
| 6,030,635 | A | 2/2000 | Gertzman et al. |
| 6,136,029 | A | 10/2000 | Johnson et al. |
| 6,139,585 | A * | 10/2000 | Li .................... 623/23.57 |
| 6,417,247 | B1 * | 7/2002 | Armstrong et al. ......... 523/115 |

FOREIGN PATENT DOCUMENTS

| | | |
|---|---|---|
| WO | WO 01/56628 A1 | 8/2001 |
| WO | WO 02/060507 A1 | 8/2002 |

OTHER PUBLICATIONS

Ito, M., In vitro properties of a chitosan-bonded hydroxyapatite bone-filling past, Biomaterials, 1991, 12(1):41-45.

Chakkalakal, et al., Adjuvant Treatment with Osteoconductive Agents in a Canine Model of Hip Reconstruction, 1995, 4:176-187.

Redepenning, et al., Characterization of electrolytically prepared brushite and hydroxyapatite coatings on orthopedic alloys, 1996, 30:287-294.

Yamaguchi, et al., Preparation and microstructure analysis of chitosan/hydroxyapatite nanocomposites, 2000, 55(1):20-27.

Hu, H. et al., "Bioactive Composite Ca-P Ceramics/Chitosan Film on Metal Surface and Electrochemical Co-Deposition Process for Preparing It", XP-002227614, (Abstract Only).

Lin, C. et al., Bioactive Composite Ca-P Ceramics/Chitosan Film on Metal Surface and Its Electrochemical Co-Deposition Preparation Process, XP-002227613, (Abstract Only).

International Search Report from PCT/US01/49875 dtd Feb. 11, 2003.

* cited by examiner

FIG·3

ELECTROLYTIC DEPOSITION OF COATINGS FOR PROSTHETIC METALS AND ALLOYS

This application is a Divisional of Ser. No. 10/034,805 filed Dec. 27, 2001 now U.S. Pat. No. 7,014,749 which claims benefit of 60/258,897 filed Dec. 28, 2000.

This invention was made with government support under DMR9972587 awarded by the National Science Foundation. The government has certain rights in the invention.

BACKGROUND OF THE INVENTION

The present invention relates to articles useful as prosthetic devices coated with an electrolytically deposited bio-compatible composite layer. More particularly, the present invention relates to a prosthetic device coated with an electrolytically deposited bio-compatible composite layer comprising hydroxyapatite and chitosan. The present invention also relates to a process for electrolytically depositing a bio-compatible composite layer on an article.

When a bone is fractured or otherwise severely damaged, it may be necessary to fixate all or a part of the bone to an internal metallic transplant support structure for stabilization and to facilitate proper healing. One problem encountered with the incorporation of metallic support structures in vivo is the inability of the structure to become fixated with, and attached to, natural bones. As such, the coating of metallic prostheses with calcium phosphate-type ceramic coatings or other materials has received a great deal of attention because of the apparent propensity of these coatings to accelerate bone fixation during the early stages following implantation. Calcium phosphate coatings appear to encourage the formation of a bond between living bone and the ceramic material and promote tissue growth which improves implant stability and longevity. Further, by various attachment mechanisms, calcium phosphate coatings appear to facilitate the transfer of functional stresses across the bone/implant interface with fewer failures.

Hydroxyapatite is a calcium phosphate containing compound that constitutes a major portion of bone and teeth. The synthetic form of hydroxyapatite is known to be bio-compatible and has been shown to enhance both interfacial shear strength and bone contact when utilized with implant materials such as titanium or other conductive metal alloys. Several methods have been developed to date for depositing hydroxyapatite precursors such as brushite on substrates including, for example, plasma-spraying, sputtering, electrophoresis, and dipping and spray pyrolysis. Precursors such as brushite are easily converted to the more stable hydroxyapatite by treatment in a caustic solution.

The clinical success of hydroxyapatite coatings deposited on metallic substrates is directly related to the chemical and mechanical stability of these coatings in vivo, as well as adhesion characteristics. To date, there have been conflicting reports on the chemical and mechanical stability of hydroxyapatite coatings in vivo. It appears that neat hydroxyapatite coatings may be subject to coating resorption and degradation over time which may negatively effect adhesion and interfacial shear characteristics. The degradation of the properties of hydroxyapatite coatings in vivo may be directly related to the non-dense, porous surface structure the hydroxyapatite coating forms on the metallic substrate during conversion from crystalline brushite. This porous surface structure may contain numerous defect areas or voids due to its plate-like surface structure which lacks a high density. It is believed that the low density and porous structure may lead to surface flaws in the hydroxyapatite coating during use in vivo and lead to the problems discussed above.

As such, a need exists for an improved coating for use on substrates suitable for implantation which will foster bone and tissue growth at the substrate surface while having improved adhesion and stability characteristics.

SUMMARY OF THE INVENTION

Among the objects of the present invention, therefore, are the provision of an article useful as a prosthetic device having a bio-compatible coating with improved adhesion characteristics; the provision of an article useful as a prosthetic device having a bio-compatible coating with improved chemical and mechanical stability; the provision of an article useful as a prosthetic device having a bio-compatible coating comprising chitosan; and the provision of an electrolytic process for producing an article having a bio-compatible composite coating electrolytically deposited thereon.

Briefly, therefore, the present invention is directed to an article having a composite layer electrolytically deposited thereon. The composite coating is comprised of a calcium phosphate compound and chitosan.

The invention is further directed to an article having a composite layer electrolytically deposited thereon. The composite coating is comprised of hydroxyapatite and chitosan.

The invention is further directed to a method of electrolytically depositing two species simultaneously as a composite coating on an article. The composite coating comprises a mixture of a calcium phosphate containing compound and chitosan. The method comprises first introducing a cathode and an anode into an electrolytic apparatus wherein the cathode comprises the substrate to be coated. An electrolyte solution is introduced into the apparatus such that it contacts both the cathode and the anode. The electrolyte solution comprises calcium ions, phosphate ions, and chitosan ions. Finally, a current is passed between the anode and the cathode to promote growth of the composite coating on the cathode.

The invention is further directed to a method of electrolytically coating an article with a composite layer which comprises a mixture of calcium phosphate and chitosan. The process comprises introducing a cathode and an anode into an electrolytic apparatus wherein the cathode comprises the substrate to be coated. A first electrolyte solution comprising calcium ions and phosphate ions is introduced into the apparatus and a current is passed between the anode and the cathode to promote the growth of a calcium phosphate containing compound on the cathode. A second electrolyte solution comprising chitosan is then introduced into the apparatus and current is again passed between the cathode and the anode to promote the growth of a chitosan containing layer on top of the calcium phosphate containing layer.

Other objects and features of this invention will be in part apparent and in part pointed out hereinafter.

DETAILED DESCRIPTION OF THE PREFERRED EMBODIMENTS

In accordance with the present invention, it has been discovered that a significant improvement in the adhesion and chemical and mechanical stability of electrolytically applied bio-compatible coatings to prosthetic devices can be achieved by providing a composite coating containing a calcium phosphate compound and chitosan. The calcium phosphate compound contained in the composite coating may initially be in one or more forms including brushite, monetite, or amorphous calcium phosphate. After electrolytically depositing the chitosan and calcium phosphate compound onto the prosthetic device, the composite coating is subjected to a basic solution to convert the calcium phosphate containing compound to hydroxyapatite. The resulting electrolytically deposited hydroxyapatite/chitosan coating exhibits bio-compatible properties and improved strength and stability. It appears that the chitosan portion of the composite layer masks or "fills in" vacancies and/or defects in the hydroxyapatite porous, plate-like structure and may provide a type of masking which improves the overall density of the resulting coating and masks the numerous defects on the surface resulting in improved properties of the coating. Although discussed primarily herein as a coating comprised of brushite, it should be understood that the calcium phosphate compound co-deposited with chitosan in accordance with the present invention can be primarily comprised of, or include, monetite, portlandite, amorphous calcium phosphate and/or whitlockite.

Figure 1:
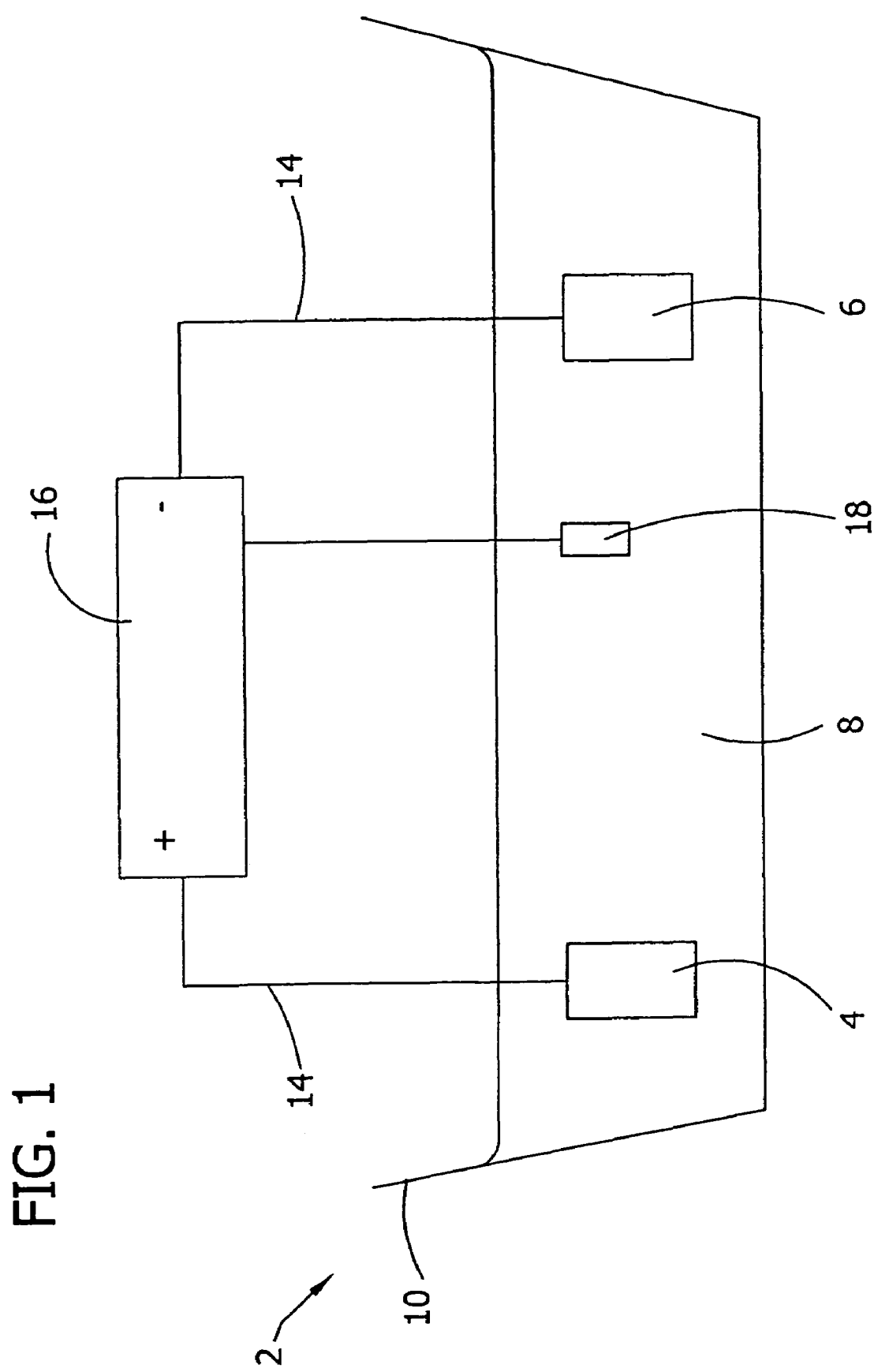
FIG. 1 is a diagram of a conventional electrolytic apparatus.
Figure 2:
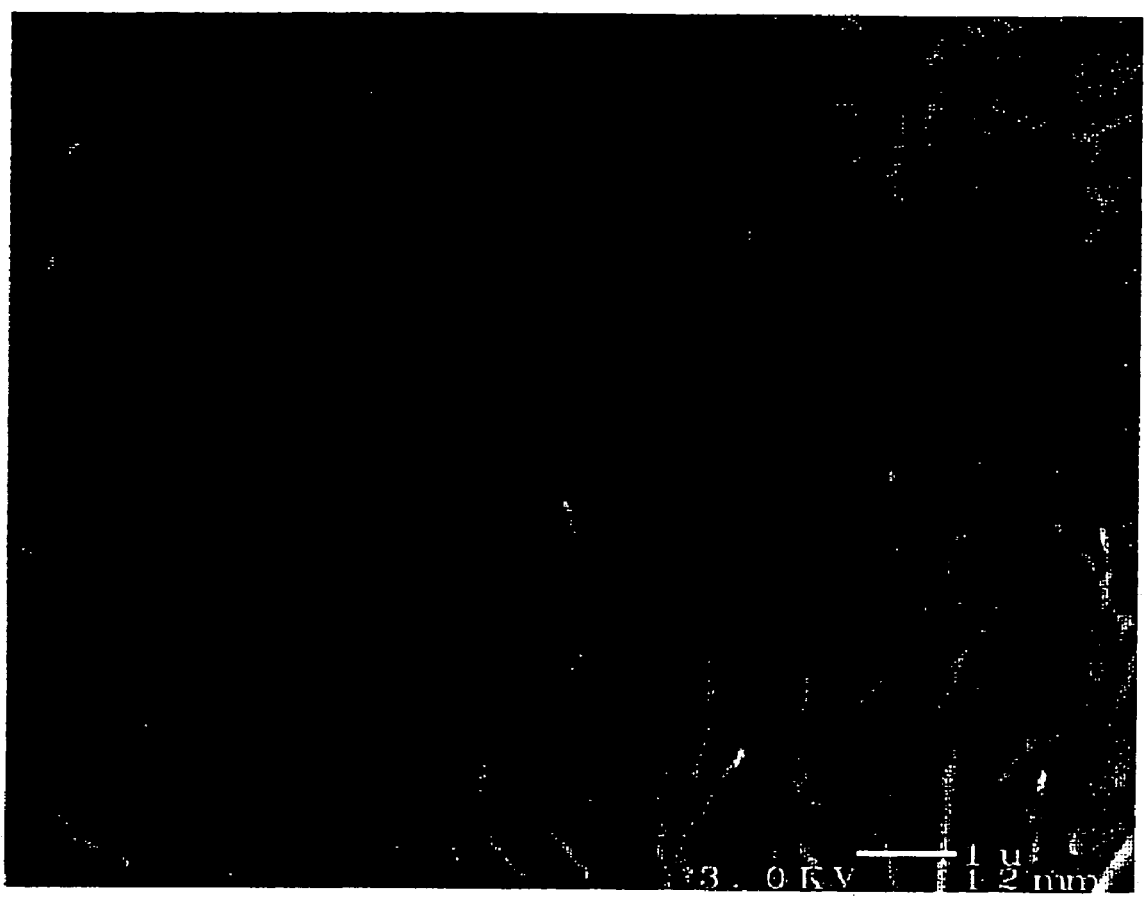
FIG. 2 is an SEM micrograph of a brushite coating deposited on a titanium substrate at 100 mA/cm$^2$.

Referring now to the Figures, and particularly to FIG. 1, there is shown a conventional electrolytic apparatus 2 which may be used in the process of the present invention to produce articles having an electrolytically deposited composite layer. The apparatus 2 comprises an anode 4, a cathode 6, electrolyte solution 8, a container 10, wiring 14, a potentiostat/gavanostat 16, and a reference electrode 18. In accordance with the present invention, the conventional apparatus is set up such that the article to receive the composite coating, i.e., the prosthetic device, is the cathode. The cathode may comprise an electrically conductive material such as a metal or metal alloy. Conductive materials which may be used as the cathode in accordance with the present invention include titanium, zirconium, hafnium, vanadium, niobium, tantalum, tin, cobalt, aluminum, chromium, molybdenum, tungsten, titanium vanadium aluminum alloys, cobalt chromium molybdenum alloys, and combinations thereof. A preferred cathodic material is titanium-aluminum(6)-vanadium (4) (6% aluminum, 4% vanadium, 90% titanium). The cathode may be in the form of a cylindrical rod, a bead, or may be irregularly shaped such as in a mesh form. When in the form of a mesh, the substrate provides an improved anchor for bony ingrowth and tissue growth.

In a preferred embodiment, the cathode is polished, cleaned, and degreased prior to contact with the electrolyte solution in the electrolytic apparatus. Several conventional procedures for polishing, cleaning, and degreasing are well known in the art and as such do not merit substantial discussion herein. One suitable conventional polishing process includes coarse grinding and subsequent polishing with a suitable polishing slurry. A suitable conventional cleaning process may comprise scrubbing the cathode with an alkaline detergent and immersing the electrode in an ultrasonic bath filled with alkaline detergent and subjecting the cathode to ultrasonic waves for a period of up to about 2 hours. Finally, a suitable degreasing process includes first rinsing the cathode with acetone and then with ethanol to produce a clean surface suitable for coating growth. It will be recognized by one skilled in the art that the anode may be subjected to a similar process to improve performance in the electrolytic apparatus.

In one embodiment of the present invention, after polishing, cleaning, and degreasing the cathode is subjected to a process to produce a thin carbon or nitride coating on the surface to reduce or eliminate the surface reactivity of the cathode with subsequent coatings. Although not generally significant, such surface reactions may effect the adhesion of subsequent calcium phosphate and/or chitosan coatings. Common techniques such as chemical vapor deposition techniques may be utilized by one skilled in the art to produce carbon or nitride coatings. Typically, the carbon or nitride coating may be from about 100 nanometers to about 100 micrometers thick, more preferably from about 5 micrometers to about 100 micrometers thick, and still more preferably from about 10 micrometers to about 50 micrometers thick. It will be recognized by one skilled in the art that although the carbon, nitride, and composite coatings of the present invention are consistently referred to herein as growing or being deposited directly onto the cathode surface which may be comprised of titanium, for example, the outermost surface of the electrode is generally in the form of an oxide, i.e., titanium oxide. As such, the coating is actually deposited on an oxide layer covering the electrode. Deposition of the coatings of the present invention onto an oxide or other thin layer on the cathode do not adversely effect coating performance.

The material of construction for the anode is not critical and may be, for example, a platinum basket, platinum foil, carbon rod, carbon plate or another substantially inert conductor that serves to complete the electrochemical circuit by facilitating oxidation reactions which complement the reduction reactions occurring at the cathode. An anode with a surface area approximately equal to or greater than that of the cathode is preferred but not required. Suitable conventional anodes are well documented in the literature. In a preferred embodiment, the external surface area of the platinum is approximately equal to the external surface area of the cathode to be coated. Additionally, in another preferred embodiment the shape of the anode is approximate to the shape of the cathode.

The electrolyte solution in the electrolytic apparatus comprises the species to be electrolytically deposited as a composite layer on the cathode. The electrolyte solution is introduced into the apparatus at a level sufficient to contact the portion of the cathode to be coated, as well as the anode. The electrolyte is typically prepared such that the resulting pH of the electrolyte solution comprising the species to be deposited on the cathode prior to the passing of the current between the anode and the cathode is typically from about 1.5 to about 7, more preferably from about 1.5 to about 5, and most preferably from about 2 to about 4. Typically, if the pH of the electrolyte is less than about 1 such that the electrolyte is highly acidic, the electrolyte solution tends to re-dissolve the deposit on the cathode as it grows resulting in little, if any, usable coating. Further, at such an acidic pH the buffering effect of the electrolyte solution due to its phosphate ion content is very high and the pH at the cathode surface may not be able to reach the necessary level for successful precipitation of brushite and/or chitosan.

In accordance with the present invention, a bio-compatible composite layer comprising a calcium phosphate compound and chitosan is deposited on the cathode from the precipitation of ionic species in the electrolyte solution. The calcium phosphate compound is typically deposited on the cathode in the form of brushite ($CaHPO_4 2H_2O$). One skilled in the art will recognize, however, that other forms of calcium phosphate such as monetite ($CaHPO_4$), whitlockite ($Ca_3(PO_4)_2$), amorphous calcium phosphate or portlandite ($Ca(OH)_2$), or a combination thereof, may also be present on the cathode after deposition. Without being bound to a particular theory, it appears that the brushite coating, as well as one or more of the other calcium or calcium phosphate containing coatings, forms as an adhesive coating on the cathode due in part to the effects of ionic migration and electrophoresis, as well as electrostatically attracted calcium ions on the cathode which may act as sites for crystallization.

The electrolyte solution for depositing a composite layer comprising brushite and chitosan on a substrate may be prepared by the mixing of two separate components; one component containing the calcium phosphate species and the other component containing the chitosan. Typically, the calcium phosphate component of the electrolyte solution may be prepared by introducing a calcium phosphate compound, such as di-protic calcium phosphate ($Ca(H_2PO_4)_2$), mono-protic calcium phosphate ($Ca(HPO_4)$), or the like into water, preferably deionized water in an amount sufficient to create from about a 0.05 molar solution of calcium phosphate to a 1 molar solution of calcium phosphate. The calcium phosphate/water mixture is stirred for several minutes to several hours to substantially dissolve the calcium phosphate compound. After mixing, any precipitate is filtered off and discarded and the clear solution used as the calcium phosphate containing component of the electrolyte solution. This produces a solution comprising calcium ions ($Ca^{2+}$), hydrogen ions ($H^+$), dihydrogen phosphate ions ($H_2PO_4^-$), monohydrogen phosphate ions ($HPO_4^{2-}$), phosphoric acid ($H_3PO_4$), and phosphate ions ($PO_4^{3-}$). One skilled in the art would recognize that other calcium phosphate containing compounds could also be used to prepare the calcium phosphate component of the electrolyte solution with similar results.

The chitosan containing component of the electrolyte solution may be prepared, for example, by mixing chitosan and a weak acid, such as acetic acid, in water. As used herein, "chitosan" refers to substantially deacetylated chitin, typically at least about 60% deacetylated, more preferably at least about 70% deacetylated, and still more preferably at least about 80% deacetylated. The chemical structure of chitin is generally shown as:

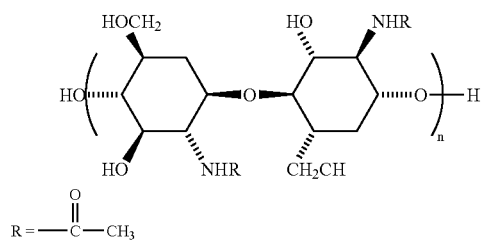

Chitosan is simply the substantially deacetylated form of chitan wherein the acetyl group on the number 3 carbon is substantially removed. The chitosan/acid solution utilized as the chitosan containing component for the electrolyte solution is typically prepared such that the resulting pH of the component is from about 1 to about 7.0. At this pH range, the chitosan is protonated and readily dissolves into solution. The chitosan containing electrolyte component will typically have between about 0.10% and about 10% chitosan (by weight) and between about 0.1% and about 5% acid (by weight) in water, which results in from about a $6 \times 10^{-3}$ M solution of chitosan to about a 0.7 M solution of chitosan.

To prepare the electrolyte solution containing both calcium phosphate and chitosan, the calcium phosphate containing component and the chitosan containing component are mixed together. Preferably, the resulting concentration of calcium phosphate is from abut 0.1 M to about 1 M and the resulting concentration of chitosan (by weight) in the electrolyte solution is from about 0.02% to about 5% (about $1.2 \times 10^{-3}$ M to about 0.3 M), more preferably from about 0.1% to about 1%. As mentioned above, the resulting pH of the electrolyte solution is from about 1.5 to about 7, preferably from about 1.5 to about 5, and most preferably from about 2 to about 4.

Once the cathode and the anode have been placed in the electrolytic apparatus and the electrolyte containing the calcium phosphate and chitosan species has been introduced into the apparatus such that it contacts the anode and cathode, a current is passed between the anode and the cathode to cause deposition of the species in the solution adjacent the cathode resulting in the growth of the composite layer on the cathode. During the operation of the current, the substrate to be coated, acting as the cathode, is made sufficiently negative such that the predominant reaction at the cathode in solution is the reduction of water to form hydrogen gas and hydroxide ions according to equation (1):

$$2H_2O + 2e^- = H_2 + 2OH^- \qquad (1)$$

The rate of the reduction of water according to equation (1) can be controlled by the amount of current (current per unit electrode area) passed between the anode and the cathode. By increasing the current density, the concentration of hydroxide ions and thus the pH at and in close proximity to the cathode surface can be increased. The localized pH increase creates a supersaturated local condition around the cathode causing less soluble species to precipitate from the solution and adhere to the cathode. In a calcium phosphate containing solution, one consequence of an increase in pH is the reaction of the monobasic phosphate ions in the solution with the hydroxide ions at or near the cathode surface according to equation (2):

$$OH^- + H_2PO_4^- <=> HPO_4^{2-} + H_2O \qquad (2)$$

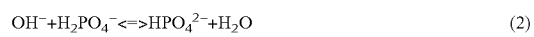

The dibasic phosphate ions produced in solution according to equation (2) quickly react with calcium ions at or near the cathode surface and precipitate out of solution onto the cathode, typically in the form of brushite according to equation (3):

$$Ca^{2+} + HPO_4^{2-} + 2H_2O <=> CaHPO_4 \cdot 2H2O \qquad (3)$$

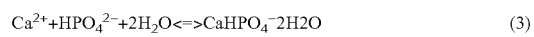

At the same time that the calcium phosphate compounds are precipitating out of solution on the cathode as current is being passed between the anode and the cathode, chitosan in the electrolyte solution is undergoing a similar precipitation according to equation (4):

$$chitosanH^+ + OH^- <=> chitosan + H_2O \qquad (4)$$

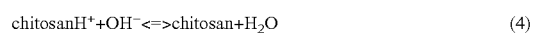

Thus, as current is passed between the anode and the cathode, a simultaneous deposition of a calcium phosphate compound, generally brushite, and chitosan are deposited onto the cathode. One skilled in the art will recognize that the hydroxide ions liberated during the electrolysis of water could also react with other species present in the electrolyte solution to produce other forms of calcium or calcium phosphate compounds including monetite, whitlockite, amorphous calcium phosphate and portlandite which may precipitate onto the cathode, or which may simply form a precipitate in solution.

Typically, composite coatings wherein the separate species are deposited simultaneously can be deposited on the cathode utilizing a current density of from about 1 mA/cm$^2$ to about 1 A/cm$^2$, preferably from about 10 mA/cm$^2$ to about 100 mA/cm$^2$ at temperatures from about 10° C. to about 60° C. As the current density is increased, the rate of electrolysis of water molecules to hydroxide ions and hydrogen gas at or near the cathode surface increases resulting in a greater increase in the pH. This result translates into quicker coating growth. The time that the current is passed between the anode and the cathode is dependent upon the current density and the desired thickness of the resulting composite layer. At lower current densities, the current may be passed for several hours, while at higher densities, a sufficient composite coating may be grown in as little as a few seconds to a few minutes. Composite coatings grown in accordance with the present invention are typically at least about 5 micrometers thick, more preferably at least about 10 micrometers thick, and still more preferably at least about 25 micrometers thick.

The calcium phosphate/chitosan containing composite coatings of the present invention typically contain at least about 1% chitosan and more preferably at least about 10% chitosan. The incorporation and intermingling of chitosan in the resulting composite coating on the cathode reduces the amount of surfaces defects found in a neat brushite or hydroxyapatite coating by "filling in" surface voids or defects found in the porous plate-like structure of brushite or hydroxyapatite after conversion from brushite described below. The chitosan also appears to increase the overall density of the composite layer resulting in a stronger coating which is less likely to fracture or otherwise fail during use in vivo. It will be recognized by one skilled in the art that the concentration of chitosan in the electrolyte solution can be varied along with other variables described herein to produce composite coatings containing a suitable amount of chitosan.

Once the co-deposition of the brushite and chitosan onto the cathode is complete, the cathode is typically subjected to a separate process to convert the brushite portion of the composite coating to hydroxyapatite ($Ca_{10}(PO_4)_6(OH)_2$). Hydroxyapatite coatings are typically more stable than brushite coatings at pH levels above about 6.9, and are the preferred form of calcium phosphate bio-compatible coatings. To convert the brushite to hydroxyapatite, the coated cathode may be subjected to a basic solution such as sodium hydroxide, potassium hydroxide or sodium phosphate. The conversion of brushite to hydroxyapatite is known in the art and proceeds according to the equilibrium reaction of equation (5):

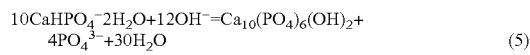

$$10CaHPO_4 \cdot 2H_2O + 12OH^- = Ca_{10}(PO_4)_6(OH)_2 + 4PO_4^{3-} + 30H_2O \quad (5)$$

In a typical conversion process, the cathode is introduced into a heated basic solution and allowed to react for several hours. Specifically, the coated cathode can be introduced into a 0.1 M sodium hydroxide solution at 100° C. and allowed to react from about 5 hours to about 24 hours or longer to complete the conversion to hydroxyapatite. Alternatively, a basic solution at room temperature may be utilized to convert the brushite to hydroxyapatite. One skilled in the art will recognize that the molar concentration of the basic solution, the chemical composition of the basic solution, the temperature and the time can be varied while still achieving the desired conversion of brushite to hydroxyapatite. Alternatively, the time, pH and/or temperature can be reduced to produce amorphous calcium phosphate deposits.

The above-described process produces a substrate having electrolytically deposited thereon a composite coating comprising hydroxyapatite and chitosan. This composite coating including chitosan exhibits superior strength and stability as compared to heretofore known electrolytically deposited coatings. This improved coating exhibits an increased density having a decreased amount of void areas on the coating surface.

In an alternative embodiment of the present invention, the composite coating comprising brushite (and ultimately hydroxyapatite after basic conversion) and chitosan can be deposited onto the substrate in two separate, distinct steps utilizing two different electrolyte solutions. Suitable substrates include those as set forth above.

In this embodiment, the electrolytic apparatus is set up with the anode, cathode, and electrolyte solution as described above with the exception that the electrolyte solution initially is comprised solely of a calcium phosphate containing solution and does not contain any chitosan. A suitable calcium phosphate containing electrolyte solution can be prepared as described above by mixing, for example, di-protic calcium phosphate and water followed by the filtering off and discarding of the precipitate. A suitable calcium phosphate solution is from about 0.05 M to about 1M. After the calcium phosphate containing electrolyte solution is introduced into the apparatus, current is passed between the anode and the cathode at a density of between about 1 mA/cm$^2$ to about 1 A/cm$^2$ for from about 30 seconds to about 50 minutes to deposit a brushite coating on the cathode as described above. For example, a suitable brushite coating may be deposited on the cathode at a current density of about 10 mA/cm$^2$ for about 9 minutes. Brushite coatings prepared in this embodiment typically have a thickness of at least about 10 micrometers, and more preferably at least about 20 micrometers. After the brushite coating is deposited onto the cathode, the cathode is removed from the electrolytic apparatus and subjected to a process as described above to convert the brushite to hydroxyapatite.

After the brushite coating has been converted to hydroxyapatite, the substrate is again introduced into the electrolytic apparatus. An electrolyte solution comprising chitosan is introduced into the apparatus, which has preferably been drained of the first electrolyte. A suitable chitosan containing electrolytic solution may be prepared by introducing chitosan and a weak acid into water. Typically the chitosan containing solution contains from about 0.1% to about 2.5% (by weight), preferably from about 0.1% to about 0.5% (by weight) chitosan and from about 0.1% to about 5% (by weight) acid, such as acetic acid, in water to produce from about a 6×10$^{-3}$ M to about a 0.16 M solution of chitosan. This second electrolyte may or may not contain calcium phosphate ions. Generally, if calcium phosphate ions are present in the second electrolyte, a higher concentration of chitosan may be utilized in the electrolyte solution. After preparation of the second electrolyte solution, current is passed between the anode and the cathode and a second layer, comprising chitosan, is grown on the brushite layer on the cathode as described above. Generally, a current density of between about 1 mA/cm$^2$ and about 1 A/cm$^2$ is sufficient to deposit the chitosan layer. Current is passed between the anode and the cathode for a period of from about 10 seconds to about 40 minutes to deposit the chitosan on the hydroxyapatite. Because the hydroxyapatite coating is crystalline and porous and contains numerous defects and void regions, the chitosan does not form a separate, distinct, second layer, but instead becomes intermingled with the hydroxyapatite in the porous structure and forms a composite layer as described above. The composite layer is inseparable, and acts as a single, intermingled composite layer as if the hydroxyapatite and chitosan were deposited simultaneously. The resulting composite layer typically has a thickness of at least about 5 micrometers, more preferably at least about 20 micrometers. One skilled in the art will recognize that the substrate having the composite layer deposited thereon utilizing a two-step process outlined above, may first have a carbon or nitride-type layer deposited on the substrate as discussed above.

In another embodiment of the present invention, the composite coating comprising hydroxyapatite and chitosan can be deposited onto the substrate in two separate steps utilizing the two step process as described above with the exception that the brushite coating is not converted to hydroxyapatite until after the chitosan is deposited onto the cathode. In this embodiment, the electrolytic apparatus is set up comprising the cathode, anode, and electrolyte as described above. The electrolyte first comprises a calcium phosphate solution without any chitosan. A coating of brushite is deposited onto the cathode utilizing the first electrolyte as described above. After a brushite coating is deposited onto the cathode, the electrolyte is changed to a second electrolyte comprising chitosan, and a second layer is deposited. This second electrolyte may or may not contain calcium phosphate ions. As discussed above, the second layer does not form a separate, distinct layer but becomes intermingled with the first layer of brushite. After the chitosan containing layer is deposited onto the cathode, the cathode is subjected to a process as described above to convert the brushite to hydroxyapatite to form a composite layer on the cathode comprising hydroxyapatite and chitosan.

In an alternative embodiment, the composite coating comprising hydroxyapatite and chitosan can be deposited onto a substrate using only a single electrodeposition step to deposit the brushite onto the article. First, brushite is electrodeposited onto a substrate as described above. Once a suitable brushite coating is present on the substrate, the substrate is removed from the electrolyte and dried. After drying, chitosan is introduced onto the brushite-coated article in the form of an aqueous chitosan-containing solution. A suitable concentration of chitosan in the aqueous solution is from about 0.1% (by weight) to about 5% (by weight) chitosan or more. The aqueous solution of chitosan can be applied to the article by, for example, dripping or spraying the aqueous solution onto the article to achieve a volume of chitosan applied to the article of from about 10 microliters/cm$^2$ to about 200 microliters/cm$^2$. The volume of chitosan can be added onto the article in one aliquot, or in several aliquots over an extended period of time.

Once the aqueous chitosan solution has been applied to the article, the water is evaporated off of the article leaving a chitosan residue intermixed with the brushite as described above to produce a composite coating in accordance with the present invention. The water from the aqueous chitosan solution can be evaporated at room temperature, or at an elevated temperature to speed the evaporation process. After the water has been evaporated, the brushite/chitosan composite coating is converted to hydroxyapatite/chitosan utilizing a basic solution as described above.

Alternatively, a composite coating can be grown on an article in accordance with the present invention utilizing a single electrodeposition step and an aqueous solution of chitosan wherein the electrodeposited brushite coating is converted to hydroxyapatite as described herein prior to the application of the aqueous chitosan solution. In this embodiment, the chitosan residue remaining after evaporation of the water is intermixed directly with the hydroxyapatite as the conversion from brushite to hydroxyapatite occurs prior to the introduction of the chitosan solution.

In a still further embodiment, the aqueous chitosan solutions described herein and used to coat a brushite or hydroxyapatite coating can contain additives such as growth factors that promote bone formation and growth. For example, the transforming growth factor-β1 (TGF-β1), which is a growth factor known to increase osteoblast proliferation and the rate of bony ingrowth on hip implants, can be introduced into the aqueous chitosan solution and deposited simultaneously onto the brushite-coated article. Composites comprising hydroxyapatite, chitosan, and TGF-β1 are particularly preferred as they provide a method of introducing growth factors into bones at known dosages while controlling the rate of release of the growth factor. A suitable amount of growth factor is, for example from about 0.05 micrograms/200 microliters of solution to about 5 micrograms/10 microliters of solution.

The present invention is illustrated by the following examples which are merely for the purpose of illustration and is not to be regarded as limiting the scope of the invention or manner in which it may be practiced.

EXAMPLE 1

In this Example, a substrate was first electrolytically coated with brushite and subsequently electrolytically coated with a layer of chitosan. After the chitosan was deposited, the brushite was converted to hydroxyapatite to produce a substrate having deposited thereon a composite coating comprising hydroxyapatite and chitosan.

An electrolytic apparatus was set up comprising a potentionstat/galvanostat (PAR Model 273) to control to current density between the anode and cathode during coating, an anode made of a platinum basket, and a cathode comprising titanium (99.7%) for depositing a bio-compatible layer thereon. Prior to insertion into the electrolytic apparatus, the cathode was subjected to a grinding process comprising coarse grinding the cathode surface with sandpaper (600 grit) followed by double polishing the surface with alumina (3.0 microns size followed by 0.3 microns size.) After the grinding/polishing, the cathode was cleaned by scrubbing the surface with a dilute sodium hydroxide solution and immersing the electrode in an ultrasonic wave apparatus for about 5 minutes. Finally, the cathode was degreased by first rinsing in acetone (99.5%) and then ethanol (99.5%) and air dried.

A first electrolyte solution containing calcium phosphate was prepared by mixing di-protic calcium phosphate (20.0 grams) in deionized water (100 mL). The mixture was vigorously agitated for two hours and the precipitate filtered off and discarded. The remaining liquid was used as the first electrolyte.

Once the apparatus was filled with the first electrolyte, current was passed between the anode and the cathode (100 mA/cm$^2$) for a period of about 5 minutes to grow a coating of brushite about 20 micrometers thick on the cathode. FIG.

2 shows an SEM micrograph of the brushite coated titanium cathode obtained at 100 mA/cm². The micrograph clearly shows the brushite in the form of a crystalline and plate-like structure with varied dimension and density.

After the brushite coating was deposited onto the cathode, the electrolyte solution was removed from the apparatus and replaced with a second electrolyte solution comprising chitosan (2.5% by weight) and acetic acid (5% by weight) in water (0.16 M solution of chitosan). A current was passed between the anode and the cathode (10 mA/cm²) for about 60 seconds to deposit a chitosan coating onto the brushite coating on the cathode.

After the deposition of the chitosan coating, the cathode was removed from the electrolytic apparatus and soaked in a solution of sodium hydroxide (0.1M) at room temperature for about 72 hours to convert the brushite to hydroxyapatite. This resulted in a coating of hydroxyapatite and chitosan on the titanium substrate. The composite layer had a thickness of about 15 micrometers.

Figure 3:
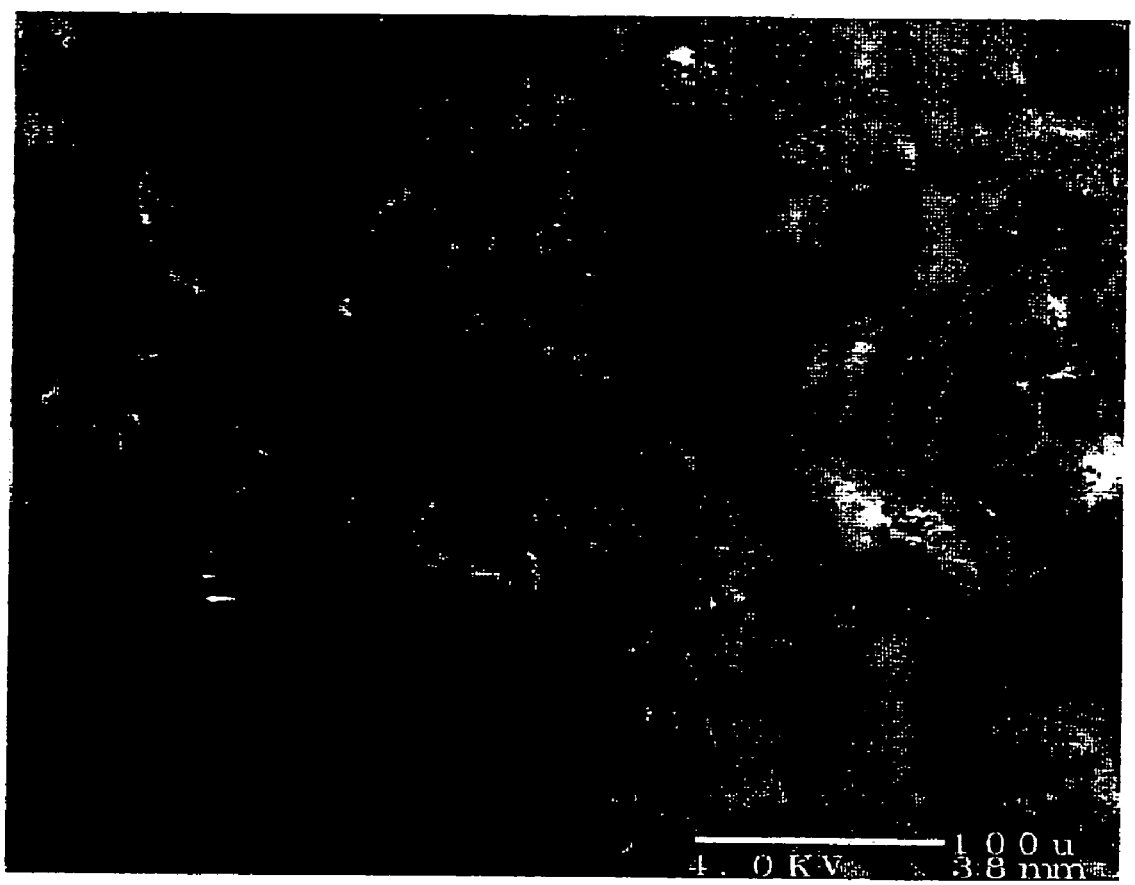
FIG. 3 is an SEM micrograph of a hydroxyapatite-chitosan coating deposited on a titanium substrate.

FIG. 3 shows an SEM micrograph of the hydroxyapatite/chitosan coated titanium substrate. It is easily seen that the chitosan clearly masks the underlying crystalline morphology of the hydroxyapatite coating and increases the overall density of the coating.

EXAMPLE 2

In this Example, a substrate had simultaneously electrolytically deposited thereon a composite coating of brushite and chitosan. After the brushite/chitosan composite coating was deposited on the substrate, the substrate was subjected to a process to convert the brushite present in the composite coating to hydroxyapatite to form a composite coating comprised of hydroxyapatite and chitosan.

An electrolytic apparatus was set up comprising a potentiostat/galvanostat (PAR Model 273) to control to current density during coating deposition, an anode made of a platinum basket, and a cathode made of titanium (99.7%) for depositing a bio-compatible layer thereon. Prior to insertion into the electrolytic apparatus, the cathode was subjected to a grinding process comprising coarse grinding the cathode surface with sandpaper (600 grit) followed by double polishing the surface with alumina (3.0 microns size followed by 0.3 microns size.) After the grinding/polishing, the cathode was cleaned by scrubbing the surface with a dilute sodium hydroxide solution and immersing the electrode in an ultrasonic wave apparatus for about 5 minutes. Finally, the cathode was degreased by first rinsing in acetone (99.5%) and then ethanol (99.5%) and air dried.

An electrolyte solution to be used during the electrolytic deposition was prepared by a two step process. First, a calcium phosphate containing solution was prepared by mixing diprotic calcium phosphate (40.0 grams) in deionized water (200 mL). The mixture was vigorously agitated for two hours and the precipitate filtered off and discarded to produce a clear solution which was utilized as the first component of the electrolyte solution. A chitosan containing solution (0.16M) was then prepared by making a solution (100 mL) containing about 2.5% (by weight) chitosan and about 5% (by weight) acetic acid in water. The calcium phosphate containing solution (200 mL) and the chitosan containing solution (10.5 mL) were then mixed together to form a calcium phosphate electrolyte containing about 0.008 M chitosan.

Once the apparatus was filled with the electrolyte, current was passed between the anode and the cathode (50 mA/cm²) for a period of about 5 minutes to co-deposit a coating of brushite and chitosan on the cathode. After the 5 minute period the current was discontinued and a composite coating of brushite and chitosan 20 micrometers in thickness was observed.

After the deposition of the composite coating comprising brushite and chitosan the cathode was removed from the electrolytic apparatus and soaked in a solution of sodium hydroxide (0.1M) at room temperature for about 72 hours to convert the brushite to hydroxyapatite. This resulted in a coating of hydroxyapatite and chitosan on the titanium substrate.

Figure 4:
FIG. 4 is an SEM micrograph of a hydroxyapatite-chitosan coating deposited on a titanium substrate.

FIG. 4 shows an SEM micrograph of the hydroxyapatite/chitosan coated titanium substrate. It is easily seen that the chitosan clearly masks the underlying crystalline morphology of the hydroxyapatite coating and increases the overall density of the coating. The adhesion and mechanical stability of the composite coating prepared in Example 2 is superior to coatings deposited without chitosan.

In view of the above, it will be seen that the several objects of the invention are achieved. As various changes could be made in the above-described electrolytic deposition process without departing from the scope of the invention, it is intended that all matter contained in the above description be interpreted as illustrative and not in a limiting sense.

What is claimed is:

1. An article comprising a substrate, the substrate having deposited thereon a second coating, said second coating comprising a mixture of a calcium phosphate compound and chitosan and said second coating having been deposited electrolytically on said substrate, wherein said substrate is the cathode in said electrolytic deposition;

wherein the substrate is selected from the group consisting of titanium, zirconium, hafnium, vanadium, niobium, tantalum, tin, cobalt, aluminum, chromium, molybdenum, tungsten, titanium vanadium aluminum alloys, cobalt chromium molybdenum alloys, and combinations thereof; and wherein the substrate is coated with a first coating selected from the group consisting of carbon and nitride prior to said electrolytic deposition.

2. An article as set forth in claim 1 wherein the calcium phosphate compound is selected from the group consisting of monetite, brushite, amorphous calcium phosphate and whitlockite.

3. An article as set forth in claim 1 wherein the carbon or nitride coating is from about 100 nanometers to about 100 micrometers thick.

4. An article as set forth in claim 1 wherein the second coating has a thickness of at least about 5 micrometers.

5. An article as set forth in claim 4 wherein the second coating has a thickness of at least about 10 micrometers.

6. An article as set forth in claim 4 wherein the second coating has a thickness of at least about 25 micrometers.

7. An article as set forth in claim 1 wherein the second coating comprises at least about 1 % chitosan.

8. An article as set forth in claim 7 wherein the second coating comprises at least about 10% chitosan.

9. An article comprising a substrate, the substrate having deposited thereon a second coating, said second coating comprising a mixture of hydroxyapatite and chitosan and said second coating having been deposited electrolytically on said substrate, wherein said substrate is the cathode in said electrolytic deposition;

wherein the substrate is selected from the group consisting of titanium, zirconium, hafnium, vanadium, niobium, tantalum, tin, cobalt, aluminum, chromium, molybdenum, tungsten, titanium vanadium aluminum alloys, cobalt chromium molybdenum alloys, and combinations thereof; and wherein the substrate is coated with a first coating selected from the group consisting of carbon and nitride prior to said electrolytic deposition.

10. An article as set forth in claim 9 wherein the carbon or nitride coating is from about 100 nanometers to about 100 micrometers thick.

11. An article as set forth in claim 9 wherein the second coating has a thickness of at least about 5 micrometers.

12. An article as set forth in claim 11 wherein the second coating has a thickness of at least about 10 micrometers.

13. An article as set forth in claim 11 wherein the second coating has a thickness of at least about 25 micrometers.

14. An article as set forth in claim 9 wherein the second coating comprises at least about 1 % chitosan.

15. An article as set forth in claim 14 wherein the second coating comprises as least about 10% chitosan.

16. The article of claim 9 comprising a prosthetic device.

* * * * *